United States Patent [19]

Wichterle

[11] Patent Number: 4,583,830

[45] Date of Patent: Apr. 22, 1986

[54] METHOD AND APPARATUS FOR MEASURING THE SHAPE OF THE EYE

[75] Inventor: Otto Wichterle, Prague, Czechoslovakia

[73] Assignee: Ceskoslovenska Akademie Ved, Prague, Czechoslovakia

[21] Appl. No.: 267,895

[22] Filed: May 28, 1981

[30] Foreign Application Priority Data

Jun. 17, 1980 [CS] Czechoslovakia ............... 4252-80

[51] Int. Cl.$^4$ ............................................. A61B 3/10
[52] U.S. Cl. .................................... 351/212; 351/221
[58] Field of Search .................. 351/13, 16, 39, 140, 351/212, 221

[56] References Cited

U.S. PATENT DOCUMENTS 3,765,753 10/1973 Zarraga ................................ 351/13
4,157,859 6/1979 Terry ................................... 351/13

Primary Examiner—Rodney B. Bovernick
Attorney, Agent, or Firm—Murray Schaffer

[57] ABSTRACT

Two plane-parallel prisms are placed in the optical axis of the examined eye, fitting close to each other in a horizontal plane lying in the optical axis. The prisms are rotated relative to one another in opposite directions at the same angle with respect to the optical axis, and having their parallel vertical optical surfaces parallel with their axis of rotation which intersects the optical axis. One prism is fixed to a scale. Two light sources are placed in a horizontal plane which passes through the optical axis and which are movable independently of one another, while their position with respect to the optical axis and to the examined eye is indicated on respectively associated scale.

4 Claims, 1 Drawing Figure

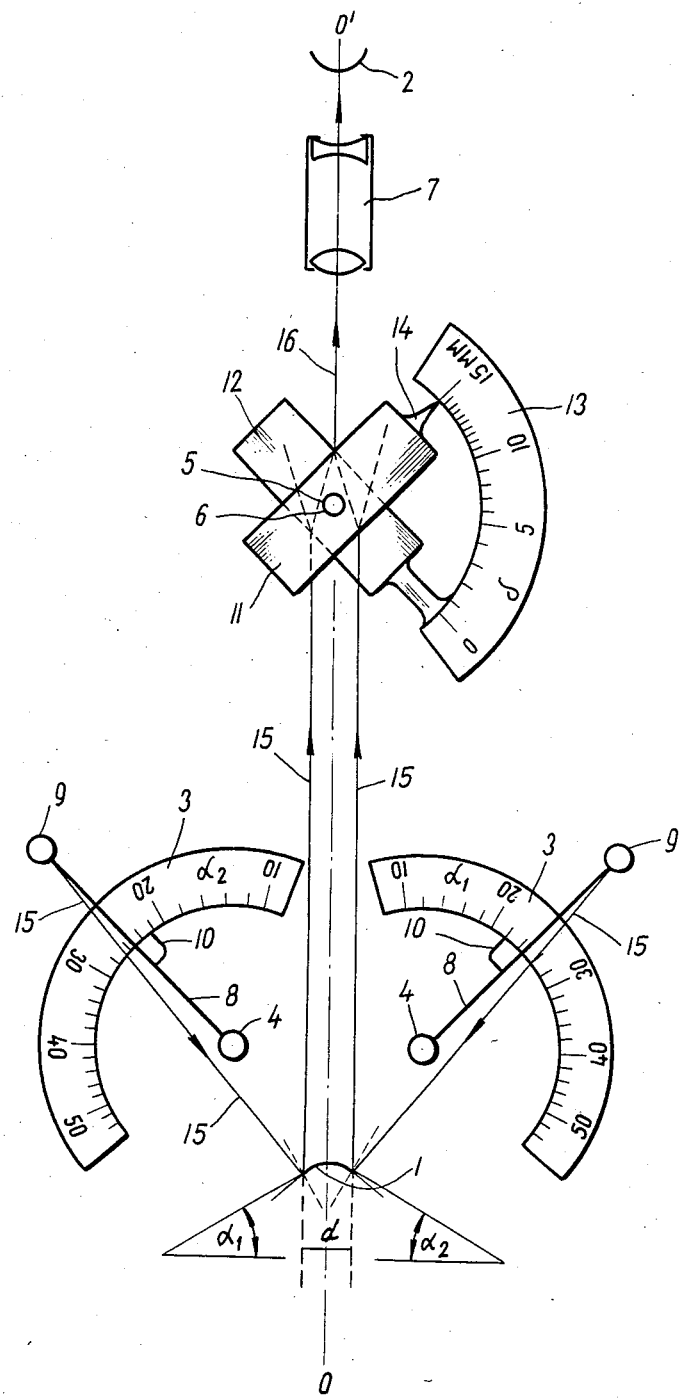

METHOD AND APPARATUS FOR MEASURING THE SHAPE OF THE EYE

The invention pertains to a method for measuring the shape of the eye by observation of relections of light sources, where the light sources move independently of one another in a horizontal plane at both sides of the optical axis of eye. The invention further concerns apparatus for performing the above method.

In the application of contact lenses, knowledge of the overall shape of the eye is of substantial importance, not only is the central corneal part of the eye of significance, but also the outside part of the organ as far as to a diameter which is at least by 2-3 mm larger than is the diameter of base of the largest contact lens is of concern. This knowledge of that enables the filter to select a contact lens, which does not exert undesirable pressures on eye. As follows, the task is to examine the shape of eye up to the diameter of 17 to 18 mm.

Till the present, the common ophthalmologic examination of the eye provided only information about the central curvature of the cornea. Also all photokeratometric methods hitherto applied described only the central part of the cornea up to the diameter of about 11 to 12 mm. The more distanced periphery of eye had been examined up till now only by lateral photography of the eye and evaluation of the pictures thus obtained. However, the measurement mediated by photographic record is rather cumbersome for the application practice because it does not give instantaneous information on the shape of the patient's eye.

For the solution of this task it may be considered that, unlike common keratometry, this case does not require measuring with an optical accuracy. Anyway, such accuracy cannot be realized because the peripheral scleral surface is covered with a wrinkled conjuctival tissue. An absolutely precise measurement of the eye shape in this region is not necessary for application of soft contact lenses, because their adaptable form manages to compensate for relatively large deviations of shape and even a relatively rough estimate of the shape type of eye is useful for the rational selection of lens.

An objective of the invention is a method for measuring the shape of eye by observation of reflections of light sources, where the light sources move in a horizontal plane at both sides of the optical axis of the eye, wherein the reflections of two light sources, movable independently of one another, are observed in the direction of the optical axis of eye and the distance between both these reflections is measured, namely in such position of the light sources where the reflection of the peripheral part of eye just appears beside the clear reflection on the surface of cornea, while the slope of eye on the places of reflections is derived from the position of light sources, and the basic parameters of the shape of eye (volumes and the sagital heights of segments of the given diameter) are derived by means of mathematical models of eye from these values as well as from the determined curvature in the center of cornea.

The method is derived from observation of the reflection of a point light source on the surface of eye. If the reflection is observed in the axis of the examined eye and the point light source is gradually shifted away from the axis, the reflection appears as a point as far as to the limbus region, but then suddenly changes into the reflection having the form of irregular line directed from the limbus far into the edge in the length of several milimeters. This tiny reflection disappears at a relatively small further shifting of the light source. It may be concluded from this observation, that the curved surface of cornea turns in the region of the limbus into a conical surface, the surface line of which has a slope similar to the marginal slope of the curved central surface of cornea.

An apparatus, for carrying out the above described method, equipped with a telescope, which axis coincides with the axis of the examined eye and the observing eye, has two plane-parallel prisms placed in the axis of the examined eye, fitting slidably close to each other in a horizontal plane lying in the optical axis, revolving contra one another in the same angle with respect to the optical axis, and having their parallel vertical optical surfaces parallel with their axis of rotation which intersects the optical axis, while one prism is fixed to a circular scale and the other prism is fixed to an indicator of this scale. Further two light sources are placed in a horizontal plane which passes through the optical axis and which are movable independently on one another, while their position with respect to the optical axis and to the examined eye is indicated on scales.

The revolving scale fitted to the prism is advantageously nonlinear according to the relationship $$d = 2t \left[ tg\delta - tg \arcsin \left( \frac{\sin\delta}{n} \right) \right] \cos\delta, \quad (1)$$

where d is the pitch of the doubled image of an object observed behind the prism, which is indicated by the scale, t is the thickness of prisms, $\delta$ is the angle included by prisms, and n is the refraction index of prisms. The light sources are advantageously movable along a horizontal circular path and their positions are indicated on coaxial circular scales, which show the slope of the eye in the location of reflection or an arbitrary mathematical function of this slope. Both light sources can be advantageously adjusted to have their end stop in an extreme position near the optical axis, while the curvature radii of the central part of eye are plotted on the circular scale with respect to this extreme position of both light sources.

The motion of both light sources can be arranged even in other way, e.g. as a translational motion in longitudinal slots along the parallelly placed scale. Also the mutual position of prisms defining the pitch of reflections needs not be read in the above given way, but it can be transformed mechanically to a differently arranged scale.

The invention is further illustrated in the drawing which shows the apparatus in the vertical direction.

The optical axis of the apparatus 0—0' coincides in the measurement position both with optical axis of patient's eye 1 and with the optical axis of observer 2. The distance of patient's eye 1 is precisely fixed with respect to the mutually fixed parts of the apparatus; these mutually immovable parts are:

(a) Two horizontal circular scales 3 fixed below the axis 0—0' at both sides and parallel with this axis. The fixed bearing 4 of revolving arms 8 is in their center.
(b) The bearings 5 and 6 to guide the optical prisms. These bearings have a common axis which is perpendicular to the axis 0—0' and intersects it.
(c) The telescope 7 in the optical axis 0—0'.

The revolving arms 8 are mounted in the bearings 4 and carry the light sources 9 which are fixed at their ends, so that each light moves during rotation of the respective arm 8 in a horizontal plane passing through the optical axis 0—0'. Also the indicator 10 pointing to the circular scale 3 is fixed to the revolving arm 8.

The glass plane-parallel prisms 11 and 12 are mounted in the bearings 5 and 6 so that the vertical axis of their rotation intersects the optical axis 0—0'. Their parallel vertical optical surfaces are parallel to their axis of rotation. The motion of both prisms is mechanically coupled by a gearing or a system of levers so that the rightward rotation of the lower prism 12 is followed up by the same leftward rotation of the upper prism 11 and vice versa. In the position where the vertical surfaces of both prisms coalesce, these surfaces stand precisely perpendicularly to the optical axis 0—0'. The circular scale 13 is fixed to the lower prism 12 and the indicator 14 revolving against the scale is fixed to the upper prism 11 so that it does not screen a viewing field around the optical axis 0—0'.

The measurement of the eye is accomplished by positioning the instrument to impinge the light sources 9 on the eye and with the telescope 7 aligned on the same horizontal plane. The light sources are then moved so that the critical position, described earlier, by which the linear light reflection from the two light sources 9 on the periphery of the eye just appears in addition to and besides the clear corneal point reflection. The slope of the linear part of the eye is then determined by following the reflections of light sources 9 on the surface of eye by the telescope 7. The angles $\alpha$, which are included by the tangents to the meridian of the cornea and the plane perpendicular to the axis of eye, may be directly read on the scales 3. The corresponding scale 3 may be easily derived from the relationship $$(a + b \cos \beta) \, tg \, (90 - 2\delta) = b \sin \beta + c \qquad (2),$$

where $\beta$ is the diversion of arm 8 from the plane connecting the axes of revolving arms 8, a is the distance of the axis of arms 8 from the axis 0—0', b is the length of arm, i.e. the distance of the light source 9 from the axis of arm, c is the distance of the plane passing through the axes of revolving arms 8 from the position of reflection on cornea.

When relative positions of prisms 11 and 12 produces doubling of the image in which the reflection on the right side of the eye overlaps with the reflection on the left side of the eye the distance of both reflections can be read on the scale 13. In this case one pair of light beams 15, coming from the light sources 9, reflected by the surface of eye 1 into the direction of optical axis coalesces into one beam 16 after passing through the prisms.

If a light reflection is observed by the ordered prisms 11 and 12 at the gradual moving of the light source 9 back from the axis 0—0', first a single reflection is visible on the optically clean surface of the cornea. As soon as the reflection reaches the region of the limbus due to further revolving of the arm 8, a reflecting light field appears at the eye periphery beside the original reflection of cornea. If the position of light is caught where this effect just appears, the reflection shows just the place where the approximately conical periphery is linked with the elliptic central part of eye. Such sites of transition, found in this way on both sides of eye, allow one to read on the scales 3 directly the slope $\alpha$ of the peripheral (conical) part of the horizontal meridian of eye on both the nasal end the temporal sides.

The revolving prisms 11 and 12 serve for the simultaneous measurement of the diameter of the transition zone, i.e. of the pitch of both reflections in the critical place. The mutual turning of prisms causes the image of both reflections in the telescope 7 to turn doubled in the horizontal direction. At a certain turn of both prisms out of their mutual angle $\delta$, the right reflection comes to the identical position with the left one. The scale 13 may then indicate, by means of the indicator 14, not only the mutual position of prisms, but directly the pitch of both reflections on the eye based on the equation (1).

This is so, since the pitch d, being the distance of the reflection between the parallel rays 15 of the two light sources, is equal to the diameter of the transition zone. The pitch d is not an angle but a length in milimeters, being in exact relationship (equation 1) to the angle included by the prisms and employed in constructing the scale 13.

The apparatus according to the invention may be also used as an ophthalmometer and allows the measurement also of the central radius of patient's eye which was stabilized in the same position. According to convention, the so called "central radius" of the eye is measured by means of reflections on the sites of 3 mm distance, assuming that the cornea is, in the center approximately spherical. In fact, the real radius is somewhat smaller due to the aspherical shape of the cornea at the center. To adapt the apparatus to this convention, it is necessary to choose such conditions when the distance of reflections is also about 3 mm. While the duplication of image and thus also the measured pitch of reflections remain constant (i.e. 3 mm) and the position of light sources changes with the keratometers of common type, it is more convenient with the described apparatus to set a constant symmetrical position of light sources and to change the duplication of image as far as the right reflection coincides with the left one. Because the central radius of almost all eyes remains within relatively narrow limits, i.e. from 7 to 8.5 mm, it can be found the setting of light sources in such angle to the optical axis, that the pitch of reflections varies very close to the value 3 mm. Then the difference between the central radius measured by the described apparatus and the value obtained by common types of ophthalmometers is several hundredths of mm at the utmost. Concerning an inferior importance of the central radius of cornea for the application of contact lenses, this accuracy is perfectly sufficient.

The apparatus according to the invention could serve also for detailed examination of topography of cornea, if a series of measurements was carried out with the gradually increasing pitch of reflections in addition to the measurement of the central radius with the reflection near the axis. However, the shape of the eye can be very well characterized by the approximation of the cornea meridian to a 2nd order curve, i.e. to an ellipse, using the values found for the reflection in the transition place, i.e. in the very proximity of limbus. If the pitch of reflections d and the average slope $tg \alpha$ were found, then the numerical eccentricity $\epsilon$ at the central radius of the eye $R_o$ is the ellipse which best fits to the shape of cornea and is defined as $$\epsilon = \sqrt{1 + \frac{1}{tg^2\alpha} - \frac{4R_0}{d^2}} \quad . \qquad (3)$$

An advantageous property of the designed apparatus consists also in the fact that the measured values of the transition radius and the slopes remain stored on scales and can be recorded and evaluated in the absence of the patient.

By means of conversion tables or simple programmable calculators, the three determined fundamental parameters of eye, i.e. the central radius, the radius of transition from the curved meridian to its linear part, and the slope of this linear part of the meridian, may be used to derive, according to the elliptical-conical model of the eye, two shape parameters of eye for each diameter of a contact lens, which have the most substantial importance for the right selection of lens; i.e. the volume and height of the equally wide segment of the measured eye. According to these two values, such soft contact lens may be then selected, which has just the required suction effect, given by a little larger volume of cavity and the same or a little larger depth than is the height of the corresponding segment of the eye, moves on the eye within the optimal limits, and does not exert undesirable pressures on eye.

I claim:

1. Apparatus for measuring the shape of the eye comprising a telescope having its axis coincident with the optical axis of the examined eye and the observer's eye, two plane-parallel prisms mounted one on top of the other and being relatively rotatable in opposite directions by the same angle with respect to the optical axis about a common axis of rotation passing perpendicularly through said optical axis, the adjacent surfaces of said prisms lying in a horizontal plane in which lies the optical axis, the parallel vertical optical surfaces of said prisms being each parallel to the axis of rotation of said prisms, a first scale fixed to one prism and an indicator for said first scale fixed to the other prism, a pair of light sources movable independently from each other in a horizontal plane passing through the optical axis on each side respectively of the optical axis, and a second and third scale for respectively determining the angular position of each light source relative to the optical axis said first scale determining the pitch between the pair of light source reflections from the examined eye.

2. The apparatus according to claim 1, wherein the first scale is nonlinear according to the relationship:

$$d = 2t\left[tg\delta - tg\arcsin\left(\frac{\sin\delta}{n}\right)\right]\cos\delta$$

where d is the pitch of the doubled image of the pair of light sources observed behind the prisms, t is the thickness of the prisms, $\delta$ is the angle included by prisms, and n is the refraction index of prisms.

3. The apparatus according to claim 1 or claim 2, wherein the light sources are movable along horizontal circular paths and the second and third scales are circular being mounted coaxially with said circular paths, the position of said light sources being indicated on the respective scale, said scales showing one of the slope of the eye in the place of reflection or an arbitrary mathematical function of this slope.

4. The apparatus according to claim 3, wherein both light sources are adjustable into an extreme position near the optical axis, while the radii of curvature of the central part of the eye are plotted on the first scale with respect to this extreme position of both light sources.

* * * * *